(12) United States Patent
Ijuin

(10) Patent No.: US 8,748,095 B2
(45) Date of Patent: Jun. 10, 2014

(54) PROBE FOR DETECTING POLYMORPHISM IN EGFR GENE AND USE OF THE PROBE

(75) Inventor: Moeko Ijuin, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 18 days.

(21) Appl. No.: 13/504,177

(22) PCT Filed: Oct. 29, 2010

(86) PCT No.: PCT/JP2010/069378
§ 371 (c)(1),
(2), (4) Date: Apr. 26, 2012

(87) PCT Pub. No.: WO2011/052754
PCT Pub. Date: May 5, 2011

(65) Prior Publication Data
US 2012/0214166 A1 Aug. 23, 2012

(30) Foreign Application Priority Data
Oct. 30, 2009 (JP) .................................. 2009-251184

(51) Int. Cl.
*C12Q 1/68* (2006.01)
*C12P 19/34* (2006.01)
*C07H 21/02* (2006.01)
*C07H 21/04* (2006.01)

(52) U.S. Cl.
USPC .......... 435/6.1; 435/91.1; 536/23.1; 536/24.3

(58) Field of Classification Search
None
See application file for complete search history.

(56) References Cited

U.S. PATENT DOCUMENTS

| | | | |
|---|---|---|---|
| 5,541,308 A * | 7/1996 | Hogan et al. ................. | 536/23.1 |
| 6,699,661 B1 | 3/2004 | Kurane et al. | |
| 8,232,051 B2 * | 7/2012 | Hirai et al. ..................... | 435/6.1 |
| 2001/0000148 A1 | 4/2001 | Kurane et al. | |
| 2001/0000175 A1 | 4/2001 | Kurane et al. | |
| 2002/0106653 A1 | 8/2002 | Kurane et al. | |
| 2003/0022177 A1* | 1/2003 | Wittwer et al. .................... | 435/6 |
| 2003/0082592 A1 | 5/2003 | Kurane et al. | |
| 2004/0063137 A1 | 4/2004 | Kurane et al. | |
| 2006/0177856 A1 | 8/2006 | Kurane et al. | |
| 2007/0026469 A1 | 2/2007 | Fuchs et al. | |
| 2008/0176226 A1 | 7/2008 | Chiou et al. | |

FOREIGN PATENT DOCUMENTS

| | | |
|---|---|---|
| EP | 1046717 | 10/2000 |
| EP | 1295941 | 3/2003 |
| JP | 2001-286300 | 10/2001 |
| JP | 2002-119291 | 4/2002 |
| JP | 2005-058107 | 3/2005 |
| JP | 2008-529532 | 8/2008 |
| WO | WO 2008/117782 | * 10/2008 |

OTHER PUBLICATIONS

NCBI NG007726 (NCBI Oct. 26, 2009).*
Paradiso et al (European Respiratory Journal vol. 32 p. 1126-1127).*
RS1050171 (NCI website DBSNP database).*
Loeffler et al., "Rapid Detection of Point Mutations by Fluorescence Resonance Energy Transfer and Robe Melting Curves in *Candida* Species." Clinical Chemistry, 46: 631-635 (2000).
Lynch et al., "Activating Mutations in the Epidermal Growth Factor Receptor Underlying Responsiveness of Non-Small-Cell Lung Cancer to Gefitinib." The New England Journal of Medicine, 350: 2129-2139 (2004).
Pao et al., "Acquired Resistance of Lung Adenocarcinomas to Gefitinib or Erlotinib Is Associated with a Second Mutation in the EGFR Kinase Domain." PLoS Medicine, 2: 225-235 (2005).
Yatabe et al., "A Rapid, Sensitive Assay to Detect EGFR Mutation in Small Biopsy Specimens from Lung Cancer." Journal of Molecular Diagnostics, 8: 335-341 (2006).
International Search Report issued in corresponding PCT Application No. PCT/JP2010/069378, mailed Nov. 30, 2010.
Extended Search Report issued in corresponding European Patent Application No. 10826884.8 dated Mar. 27, 2013.
Bernard et al., "Real-Time PCR Technology for Cancer Diagnostics," Clinical Chemistry, 48:1178-1185 (2002).
Kofiadi et al., "Methods for Detecting Single Nucleotide Polymorphisms: Allele-Specific PCR and Hybridization with Oligonucleotide Probe," Russian Journal of Genetics, 42:16-26 (2006).
Li et al., "Coamplification at Lower Denaturation Temperature-PCR Increases Mutation-Detection Selectivity of TaqMan-Based Real-Time PCR," Clinical Chemistry, 55: 748-756 (2009).
Nomoto et al., "Detection of EGFR Mutations in Archived Cytologic Specimens of Non-Small Cell Lung Cancer Using High-Resolution Melting Analysis," American Journal of Clinical Pathology, 126: 608-615 (2006).
Sasaki et al., "EGFR Mutation Status in Japanese Lung Cancer Patients: Genotyping Analysis Using LightCycler," Clinical Cancer Research, 11: 2924-2929 (2005).
Office Action issued in corresponding European Patent Application No. 10826884.8 dated Jan. 3, 2014.

* cited by examiner

Primary Examiner — Jehanne Sitton
(74) Attorney, Agent, or Firm — Morgan, Lewis & Bockius LLP

(57) ABSTRACT

The present invention provides a polymorphism detection probe that can identify a polymorphism in an EGFR gene easily and with high reliability and a polymorphism detection method using the probe. The probe of the present invention is a probe for detecting a polymorphism in an EGFR gene, including at least one of an oligonucleotide (P1) and an oligonucleotide (P2), wherein:
(P1) is a 22- to 50-mer oligonucleotide composed of a base sequence complementary to a base sequence including 334th to 355th bases in SEQ ID NO: 1 and having a base complementary to the 334th base in its 3' end region; and
(P2) is an oligonucleotide composed of a base sequence complementary to the oligonucleotide (P1).

11 Claims, 2 Drawing Sheets

PROBE FOR DETECTING POLYMORPHISM IN EGFR GENE AND USE OF THE PROBE

The present application is a U.S. National Phase Application of International Application No. PCT/JP2010/069378, filed Oct. 29, 2010, which claims the benefit of priority of Japanese Application No. 2009-251184 filed Oct. 30, 2009, the disclosures of which are incorporated herein by reference in their entireties.

Sequence Listing Submission via EFS-Web A computer readable text file, entitled "068022-5036-SequenceListing.txt" created on or about Apr. 25, 2012 with a file size of about 6 kb contains the sequence listing for this application and is hereby incorporated by reference in its entirety.

TECHNICAL FIELD

The present invention relates to a probe for detecting a polymorphism in an EGFR gene and use of the probe.

An epidermal growth factor receptor (EGFR) is a tyrosine kinase-type receptor of an epidermal growth factor (EGF). EGFR expression is observed with high frequency in many kinds of solid cancers, and it is known that the overexpression of EGFR is associated with the malignancy and prognosis of the cancers. Thus, EGFR tyrosine kinase inhibitors such as gefitinib, for example, are used as drugs for cancer treatment. However, gefitinib may fail to exhibit a therapeutic effect because some patients show resistance to gefitinib. In recent years, it has been revealed that the mutation of the EGFR is involved in this drug resistance (Pao et al., PLoS Medicine, 2005, Vol. 2, No. 3, pp. 225 to 235; and Lynch et al., New England Journal of Medicine, 2004, Vol. 350, No. 21, pp. 2129 to 2139). The mutation is such that threonine (T) as the 790th amino acid of the EGFR is substituted with methionine (M), and in the CDS of the EGFR gene, cytosine (c) as the 2369th base in exon 20 is mutated to thymine (t). Therefore, by detecting the presence or absence of this mutation, i.e., a polymorphism, in exon 20 of the EGFR gene, it is possible to determine whether or not the subject is resistant to gefitinib before conducting a treatment. This analysis allows for an efficient tailor-made cancer treatment.

On the other hand, as a method for detecting a polymorphism in a gene, various methods have been reported. Examples thereof include a PCR (Polymerase Chain Reaction)-RFLP (Restriction Fragment Length Polymorphism) method.

The PCR-RFLP method is carried out by amplifying a detection target region in a target DNA in a sample by PCR, treating the obtained amplification product with a restriction enzyme, and typing the change in restriction fragment length caused by a polymorphism according to Southern hybridization. When a target mutation is present in the gene, the recognition site of the restriction enzyme disappears. Thus, it is possible to detect the presence or absence of the mutation based on the presence or absence of cleavage, i.e., the change in restriction fragment length.

However, in the PCR-RFLP method, for example, after the PCR, it is necessary to conduct a cumbersome procedure of treating the obtained amplification product with a restriction enzyme and conducting an analysis. Furthermore, in order to treat the obtained amplification product with a restriction enzyme, the amplification product has to be temporarily taken out from a reactor. Thus, there is a risk that the amplification product obtained in a first reaction may scatter and be mixed in a second reaction that is different from the first reaction. Such problems make the automation of the polymorphism detection difficult.

In light of these problems, Tm (Melting Temperature) analysis is attracting attention in recent years as a method for detecting a polymorphism. In the Tm analysis, first, using a probe complementary to a region including a detection target polymorphism, a hybrid (double-stranded nucleic acid) of a nucleic acid to be examined (hereinafter simply referred to as a "test nucleic acid") with the probe is formed. Then, the thus-obtained hybrid is heat-treated, and dissociation (melting) of the hybrid into single-stranded nucleic acids accompanying the temperature rise is detected by measuring signals such as absorbances. By determining the Tm value based on the result of the detection, the polymorphism is determined. The Tm value becomes higher as the complementarity between the single-stranded nucleic acids of the hybrid becomes higher, and becomes lower as the complementarity between the same becomes lower. Thus, in the case where the polymorphism in a detection target site is X or Y, the Tm value of a hybrid composed of a nucleic acid containing the target polymorphism (e.g., Y) and a probe that is 100% complementary thereto is determined beforehand (the Tm value as an evaluation standard value). Subsequently, the Tm value of a hybrid composed of the test nucleic acid and the probe is measured (the Tm value as a measured value). Then, when this measured value is the same as the evaluation standard value, it can be determined that the test nucleic acid shows a perfect match with the probe, i.e., the detection target site in the test nucleic acid is the target polymorphism (Y). On the other hand, when the measured value is lower than the evaluation standard value, it can be determined that the test nucleic acid shows a mismatch with the probe, i.e., the detection target site in the test nucleic acid is the other polymorphism (X). According to such a method, a polymorphism can be detected merely by thermal-treating a PCR reaction solution containing the probe and then measuring signals, for example. Thus, it is possible to automate a detecting device.

However, in detection methods utilizing such Tm analysis, it is necessary to determine the difference in a single base from the Tm value, for example. Therefore, in particular, even in the case where a normal polymorphism and a mutant-type polymorphism are present together, for example, it is required to detect the presence or absence of mutation accurately.

BRIEF SUMMARY OF THE INVENTION

Problem to be Solved by the Invention

With the foregoing in mind, it is an objective of the present invention to provide a probe that can identify a polymorphism in an EGFR gene easily and with high reliability, and use of the probe.

Means for Solving Problem

In order to achieve the above objective, the present invention provides a probe for detecting a polymorphism in an EGFR gene, including either one of an oligonucleotide (P1) and an oligonucleotide (P2), wherein:

(P1) is a 22- to 50-mer oligonucleotide composed of a base sequence complementary to a base sequence including 334th to 355th bases in SEQ ID NO: 1 and having a base complementary to the 334th base in its 3' end region; and (P2) is an oligonucleotide composed of a base sequence complementary to the oligonucleotide (P1).

The present invention also provides a reagent for detecting a polymorphism in an EGFR gene, containing the probe of the present invention.

The present invention also provides a method for detecting a polymorphism in an EGFR gene, including the step of: detecting a polymorphism in an EGFR gene using the probe of the present invention.

Effects of the Invention

According to the probe of the present invention, a polymorphism in an EGFR gene can be identified easily and with high reliability by Tm analysis, for example. Specifically, for example, even in the case where an EGFR gene having a normal target polymorphism and an EGFR gene having a mutant-type target polymorphism are present together in a sample, the kind of polymorphism or the presence or absence of mutation can be detected easily and with high reliability by the Tm analysis using the probe of the present invention. Therefore, the present invention is particularly useful when applied to a sample containing both the wild-type (also referred to as normal) EGFR gene and a mutant-type EGFR gene. Thus, according to the present invention, a polymorphism in an EGFR gene can be identified easily and with high reliability, so that, for example, the detection result can be reflected in treatments carried out by administration of an anticancer drug, such as described above. Hence, it can be said that the present invention is very useful in a medical field and the like.

MODE FOR CARRYING OUT THE INVENTION

Figure 1A:
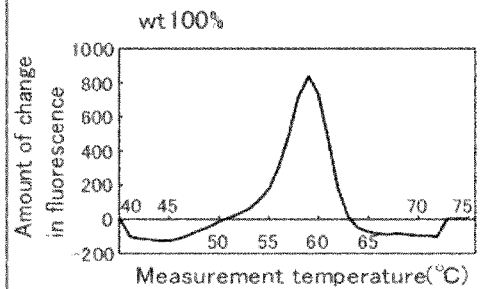
FIGS. 1A to 1C are graphs showing the results of Tm analysis obtained in Example 1 of the present invention.

In the present invention, a detection target polymorphism in the EGFR gene is the above-described polymorphism in exon 20. The polymorphism is, for example, a polymorphism at the 347th base in a partial sequence of the EGFR gene shown in SEQ ID NO: 1. The polymorphism of wild type is such that, in the partial sequence of the EGFR gene shown in SEQ ID NO: 1, the 347th base (y) is cytosine (c), and in the EGFR protein, the 790th amino acid is threonine. The polymorphism of the mutant type is such that, in the partial sequence of the EGFR gene shown in SEQ ID NO: 1, the 347th base (y) is thymine (t), and in the EGFR protein, the 790th amino acid is methionine. In the EGFR gene, when the polymorphism of the base is of the wild type, it can be determined that the subject is sensitive to tyrosine kinase inhibitors such as gefitinib, and when the polymorphism of the base is of the mutant type, it can be determined the subject is resistant to the tyrosine kinase inhibitors.

The base sequence of the EGFR gene is registered under GenBank Accession No. NG_007726, for example. In the base sequence of Accession No. NG_007726, a region from the 5001st base to 193307th base is the full-length base sequence of the EGFR gene. The base sequence of SEQ ID NO: 1 is a partial sequence of the EGFR gene, and it corresponds to a region from the 167001st base to the 168020th base in the base sequence of Accession No. NG_007726. In the base sequence of SEQ ID NO: 1, a region from the 262nd base to the 447th base is exon 20.

In the present invention, hereinafter, the EGFR gene in which the above-described base is of the mutant-type is referred to as the "mutant-type EGFR gene", and the EGFR gene in which the above-described base is of the wild type referred to as the "wild-type EGFR gene or normal EGFR gene".

In the present invention, a site at which the above-described polymorphism occurs, i.e., the 347th base in the base sequence of SEQ ID NO: 1 (sense strand) or a base to be paired with the 347th base in the sense strand in a complementary sequence thereto (antisense strand), is referred to as a "detection target site". In the base sequence of SEQ ID NO: 1 (sense strand) or in the complementary sequence thereto (antisense strand), a region including the detection target site and to which the probe can hybridize is referred to as a "hybridization region or detection target sequence". Regarding the detection target sequence, the one showing a perfect match with the probe except for an arbitrary site(s) other than the detection target site is referred to as a "perfect match sequence", and the one in which the detection target site and an arbitrary site(s) show a mismatch with the probe is referred to as a "mismatch sequence". In the present invention, a perfect match means that the base at the detection target site is complementary to a base to be paired therewith in the probe, and preferably means that the detection target sequence is perfectly complementary with the probe except for an arbitrary site(s) other than the detection target site in the detection target sequence. In the present invention, a mismatch means that the base at the detection target site is not complementary to a base to be paired therewith in the probe, and preferably means that the detection target sequence is perfectly complementary to the probe except for the detection target site and an arbitrary site(s) in the detection target sequence.

In the present invention, in the case where the EGFR gene is amplified and further, the probe of the present invention is caused to hybridize with the resultant amplification product, a region to be amplified in the EGFR gene hereinafter is referred to as an "amplification target region". The amplification target region may be, for example, a region in the sense strand of the EGFR gene, a region corresponding thereto in the antisense strand, or both of them. In the present invention, the terms "sense strand" and "antisense strand" encompass, for example, amplification products of the sense strand and amplification products of the antisense strand, respectively.

In the present invention, the ends of a base sequence mean the endmost bases on the 5' side and the 3' side in the base sequence. Furthermore, a 5' end region is a region including several bases from the 5' end in a base sequence, and a 3' end region is a region including several bases from the 3' end in a base sequence. The several bases mean, for example, 1 to 10, 1 to 4, 1 to 3, or 1 to 2 bases including the base at the end. In the present invention, the Zth base (Z is a positive integer) from an end of a base sequence is a numerical order counted with a base at the end as the first base. For example, the first base from the end means the base at the end, and the second base from the end means a base next to the base at the end.

<Probe for Detecting Polymorphism>

The probe of the present invention is, as described above, a probe for detecting a polymorphism in an EGFR gene, including at least one of an oligonucleotide (P1) and an oligonucleotide (P2), wherein:

(P1) is a 22- to 50-mer oligonucleotide composed of a base sequence complementary to a base sequence including 334th to 355th bases in SEQ ID NO: 1 and having a base complementary to the 334th base in its 3' end region; and (P2) is an oligonucleotide composed of a base sequence complementary to the oligonucleotide (P1).

The probe of the present invention is a probe for detecting a polymorphism (c/t) in the 347th base (y) in the partial sequence of the EGFR gene shown in SEQ ID NO: 1. The oligonucleotide (P1) is complementary to the sense strand of the EGFR gene, and the polymorphism can be checked through hybridization of this oligonucleotide with the sense strand. The oligonucleotide (P2) is homologous to the sense strand of the EGFR gene, and the polymorphism can be checked through hybridization of this oligonucleotide with the antisense strand.

When describing the oligonucleotides (P1) and (P2), the term "complementary" may refer to a state of perfectly complementary or a state of perfectly complementary except for an arbitrary base(s). The arbitrary base(s) is a base at a site other than a site that hybridizes to the detection target site. The number thereof is not particularly limited, and may be one, for example.

The base length of the oligonucleotides (P1) and (P2) is 22- to 50-mer, as described above. The upper limit of the base length preferably is 40-mer, more preferably 30-mer.

In the oligonucleotide (P1), a base complementary to the 347th base in SEQ ID NO: 1 is represented by r, which is adenine (a) or guanine (g).

The oligonucleotide (P1) has the base complementary to the 334th base in its 3' end region. The base preferably is any one of the 1st to 4th bases from the 3' end, more preferably any one of the 1st to 3rd bases from the 3' end, and particularly preferably the 1st base (i.e., the 3' end) or the second base from the 3' end. The oligonucleotide (P1) may be an oligonucleotide composed of the base sequence of any one of SEQ ID NOs: 2, 15, 16, and 17, for example.

```
tgagctgcrtgatgaggtgcac      (SEQ ID NO: 2)

tgagctgcrtgatgaggtgcacg     (SEQ ID NO: 15)

tgagctgcrtgatgaggtgcacgg    (SEQ ID NO: 16)

tgagctgcrtgatgaggtgcacggt   (SEQ ID NO: 17)
```

When compared to a region including the 334th to 355th bases in the base sequence of SEQ ID NO: 1, the oligonucleotides (P1) shown in SEQ ID NOs: 2 and 15 to 17 are base sequences perfectly complementary to the region except for the 17th base (g) from the 5' end. In the oligonucleotides (P1), the 9th base r from the 5' end is a base complementary to the detection target site in the sense strand, i.e., the 347th base (y) in the base sequence of SEQ ID NO: 1. The base r is adenine (a) or guanine (g).

When the 9th base r from the 5' end of the oligonucleotides (P1) shown in SEQ ID NOs: 2 and 15 to 17 is guanine (g), the oligonucleotides (P1) show a perfect match with a detection target sequence in which the 347th base (y) in the base sequence of SEQ ID NO: 1 is cytosine (c), except for the 17th base (g) from the 5' end. Furthermore, when the 9th base r of the oligonucleotides (P1) is guanine (g), the oligonucleotides (P1) show a mismatch with a detection target sequence in which the 347th base (y) in the base sequence of SEQ ID NO: 1 is thymine (t). In this case, in the oligonucleotides (P1), the 9th base (g) and the 17th base (g) show a mismatch with bases at the corresponding sites in the detection target sequence. On the other hand, when the 9th base r of the oligonucleotides (P1) is adenine (a), the oligonucleotides (P1) show a perfect match with the detection target sequence in which the 347th base (y) in the base sequence of SEQ ID NO: 1 is thymine (t), except for the 17th base (g). Furthermore, when the 9th base r of the oligonucleotides (P1) is adenine (a), the oligonucleotides (P1) show a mismatch with the detection target sequence in which the 347th base (y) in the base sequence of SEQ ID NO: 1 is cytosine (c), except for the 17th base (g). In this case, in the oligonucleotides (P1), the 9th base (a) and the 17th base (g) show a mismatch with bases at the corresponding sites in the detection target sequence. Therefore, the polymorphism in the EGFR gene can be detected based on whether or not the oligonucleotides show a perfect match with the detection target sequence in the EGFR gene.

The oligonucleotides (P1) shown in SEQ ID NOs: 2 and 15 to 17 may be oligonucleotides composed of the base sequences of SEQ ID NOs: 3, 4, and 18 to 23, for example. Among them, the oligonucleotides composed of the base sequences of SEQ ID NOs: 3, 18, 20, and 23 are preferable.

```
tgagctgcatgatgaggtgcac      (SEQ ID NO: 3)

tgagctgcgtgatgaggtgcac      (SEQ ID NO: 4)

tgagctgcatgatgaggtgcacg     (SEQ ID NO: 18)

tgagctgcgtgatgaggtgcacg     (SEQ ID NO: 19)

tgagctgcatgatgaggtgcacgg    (SEQ ID NO: 20)

tgagctgcgtgatgaggtgcacgg    (SEQ ID NO: 21)

tgagctgcatgatgaggtgcacggt   (SEQ ID NO: 22)

tgagctgcgtgatgaggtgcacggt   (SEQ ID NO: 23)
```

The oligonucleotide (P2) is complementary to the oligonucleotide (P1), as described above. In other words, the oligonucleotide (P2) is a 22- to 50-mer oligonucleotide composed of a base sequence homologous to a base sequence including 334th to 355th bases in SEQ ID NO: 1 and having the 334th base in its 5' end region. The term "homologous" may refer to a state of perfectly homologous or a state of perfectly homologous except for an arbitrary base(s). The arbitrary base(s) is a base at a site other than a site that hybridizes to the detection target site. The number thereof is not particularly limited, and may be one, for example. A specific example of the oligonucleotide (P2) is an oligonucleotide composed of a base sequence homologous to a region including the 334th to 355th bases in the base sequence of SEQ ID NO: 1 except for the 339th base (g). In the oligonucleotide (P2), the 347th base in SEQ ID NO: 1 is represented by y. The base y is thymine (t) or cytosine (c).

The probe of the present invention may be a probe including any of the above-described oligonucleotides or a probe composed of any of the above-described oligonucleotides, for example.

The probe of the present invention preferably is a labeled probe having a labeling substance. For example, it is preferable that the oligonucleotide is labeled (modified) with the labeling substance. In the oligonucleotide, a site to be labeled with the labeling substance is not particularly limited, and it preferably is a 5' end region or a 3' end region, more preferably the 5' end or the 3' end, for example. As will be described below, in the oligonucleotide, a base to be labeled with the labeling substance preferably is cytosine (c) or guanine (g), for example. The base may be labeled directly with the labeling substance, or alternatively, it may be labeled indirectly with the labeling substance, for example. In the latter case, for example, by labeling any site in a nucleotide residue containing the base, the base can be labeled indirectly with the labeling substance.

The oligonucleotide (P1) preferably has the labeling substance in its 3' end region. Specifically, the labeling substance preferably is located at a position of the 1st to 4th bases from its 3' end. It is more preferable that any base from the 1st to 4th bases from the 3' end, still more preferably any base from the 1st to 3rd bases from the 3' end, and particularly preferably the 2nd base from the 3' end or the base at the 3' end has the labeling substance, for example. In the oligonucleotide (P1), it is preferable that, for example, any of the bases complementary to the 334th to 337th bases has the labeling substance, and it is more preferable that a base (c) complementary to the 334th base has the labeling substance.

The oligonucleotide (P2) preferably has the labeling substance in its 5' end region. Specifically, the labeling substance preferably is located at a position of the 1st to 4th bases from its 5' end. It is more preferable that any base from the 1st to 4th bases from the 5' end, still more preferably any base from the 1st to 3rd bases from the 5' end, and particularly preferably the 2nd base from the 5' end or the base at the 5' end has the labeling substance, for example. In the oligonucleotide (P2), it is preferable that, for example, any of the 334th to 337th bases has the labeling substance, and it is more preferable that the 334th base (g) has the labeling substance.

The labeling substance is not particularly limited, and preferably is the one that gives off signals depending on whether the labeled probe is present independently or it forms a hybrid, for example. The kind of the signal is not particularly limited, and examples of the signal include fluorescence and coloring. The coloring may be color development or color change, for example. When the signal is fluorescence, examples of a signal value include a fluorescence intensity. When the signal is coloring, examples of a signal value include reflectance, absorbance, and transmittance. The signal may be given off from the labeling substance directly or indirectly, for example.

The labeling substance is not particularly limited, and examples thereof include fluorescent labeling substances such as a fluorophore. Examples of the fluorescent substance include fluorescein, phosphor, rhodamine, and polymethine dye derivatives. Examples of commercially available fluorescent substances include Pacific Blue® (Molecular Probes), BODIPY FL® (Molecular Probes), FluorePrime™ (Amersham Pharmacia), Fluoredite™ (Millipore Corporation), FAM® (ABI), Cy3™ and Cy5™ (Amersham Pharmacia), and TAMRA® (Molecular Probes). The detection condition for the fluorescent substance is not particularly limited, and can be determined as appropriate depending on the kind of the fluorescent substance to be used, for example. Specifically, Pacific Blue can be detected at a detection wavelength from 450 to 480 nm, for example; TAMRA can be detected at a detection wavelength from 585 to 700 nm, for example; and BODIPY FL can be detected at a detection wavelength from 515 to 555 nm, for example. When such a labeled probe is used, for example, by detecting fluorescence as a signal and measuring a fluorescence intensity as a signal value, hybridization and dissociation can be checked easily based on the change in fluorescence intensity.

Preferably, the labeled probe is, for example, a labeled probe that shows signals independently and shows no signals when it forms a hybrid, or a labeled probe that shows no signals independently and shows signals when it forms a hybrid. When the labeling substance is a fluorescent substance, the labeled probe preferably is a probe that is labeled with the fluorescent substance, shows fluorescence independently, and shows reduced (e.g., quenched) fluorescence when it forms a hybrid, for example. Such a phenomenon generally is called a fluorescence quenching phenomenon. Probes utilizing this phenomenon generally are called fluorescence quenching probes. Among these fluorescence quenching probes, preferred is the one in which the 3' end or the 5' end of the oligonucleotide is labeled with the fluorescent substance, and the base at the end to be labeled preferably is cytosine (c) or guanine (g). In the case where the base at the end is cytosine (c), the base sequence of the fluorescence quenching probe preferably is designed so that, for example, when the fluorescence quenching probe forms a hybrid with a test nucleic acid, a base to be paired with the labeled cytosine (c) at the end or a base apart therefrom by one to three bases in the test nucleic acid is guanine (g). A base away from the base to be paired with cytosine (c) by one base is a base located next to the base to be paired with cytosine (c). Such a probe generally is called a guanine quenching probe, and is known as a so-called QProbe®. When the guanine quenching probe hybridizes to the test nucleic acid, there occurs a phenomenon that, for example, as the fluorescent substance-labeled cytosine (c) at the end approaches guanine (g) in the test nucleic acid, fluorescence of the fluorescent substance becomes weak, in other words, the fluorescence intensity is reduced. By using the probe such as described above, hybridization and dissociation can be checked easily based on the change in fluorescence intensity, for example. Similarly, in the case where the above-described base at the end is guanine (g), the base sequence of the fluorescence quenching probe preferably is designed so that, for example, when the fluorescence quenching probe forms a hybrid with a test nucleic acid, a base to be paired with the labeled guanine (g) at the end or a base apart therefrom by one to three bases in the test nucleic acid is cytosine (c).

In the probe of the present invention, for example, a phosphate group may be added to the 3' end. As will be described below, a test nucleic acid can be prepared by a nucleic acid amplification method such as PCR, for example. At this time, the probe of the present invention may be caused to be present in a reaction system of the nucleic acid amplification reaction. In such a case, when the 3' end of the probe has a phosphate group added thereto, it is possible to sufficiently prevent the probe itself from being elongated by the nucleic acid amplification reaction. A similar effect is obtained also by adding a labeling substance such as described above to the 3' end of the probe.

In the detection of the polymorphism using the probe of the present invention, the detection method is by no means limited as long as it is a method utilizing the hybridization of the detection target sequence and the probe. As the method for detecting the polymorphism, the polymorphism detection method according to the present invention will be described below.

<Method for Detecting Polymorphism>

The method for detecting a polymorphism according to the present invention is, as described above, a method for detecting a polymorphism in an EGFR gene, including the step of detecting a polymorphism in an EGFR gene using the probe of the present invention.

In the method of the present invention, the detecting step preferably includes the steps of:
(A) while changing a temperature of a reaction system containing a test nucleic acid and the probe of the present invention, measuring a signal value indicating a melting state of a hybrid of the test nucleic acid and the probe; and
(B) detecting the polymorphism in the test nucleic acid based on change in the signal value accompanying the temperature change.

The method of the present invention is characterized in that it uses the probe of the present invention, and other configurations, conditions, and the like are not limited to those described below. As described above, the probe of the present invention preferably is a labeled probe. In the present invention, the reaction system is a reaction solution, for example.

In the present invention, the test nucleic acid may be a single-stranded nucleic acid or a double-stranded nucleic acid. When the test nucleic acid is a double-stranded nucleic acid, the step (A) preferably includes the step of dissociating the double-strand test nucleic acid by heating the reaction system, for example, as will be described below. By dissociating the double-stranded nucleic acid into single-stranded nucleic acids, the probe of the present invention can hybridize with the single-stranded nucleic acid.

In the present invention, the test nucleic acid may be a nucleic acid contained inherently in a sample or an amplification product of the nucleic acid, for example. The latter is preferable because, for example, it allows the detection accuracy to be improved. The amplification product can be prepared by amplifying the nucleic acid in the sample as a template nucleic acid according to a nucleic acid amplification method, for example. The amplification product may be an amplification product obtained by using DNA in the sample as a template or an amplification product obtained by using cDNA synthesized from RNA in the sample as a template, for example. Examples of the RNA in the sample include RNAs such as total RNA and mRNA, and the cDNA can be synthesized from, for example, the RNA such as described above by RT-PCR (Reverse Transcription PCR).

In the case where the test nucleic acid is the amplification product, the method of the present invention may further include the following step (X):

(X) producing the amplification product from a template nucleic acid. The step (X) preferably is performed prior to the step (A). The step (X) may be the step of producing the amplification product from the template nucleic acid in a reaction system in the presence of the probe, for example.

In the step (A), it is only necessary that the probe is contained in the reaction sysytem, and the timing of adding the probe is not particulaly limited. In the case where the test nucleic acid is the amplification product, the reaction system in the step (A) may be prepared newly using the amplification product obtained in the step (X) and the probe, or may be the reaction system of the amplification reaction in the step (X), for example. In the latter case, the probe may be added to the reaction system of the amplification reaction before or during the step (X). Alternatively, the probe may be added to the reaction system after the step (X).

The method for amplifying the nucleic acid is not particularly limited, and examples thereof include a PCR (Polymerase Chain Reaction) method, a NASBA (Nucleic Acid Sequence Based Amplification) method, a TMA (Transcription-Mediated Amplification) method, and a SDA (Strand Displacement Amplification) method. Among them, the PCR method is preferable. The conditions of the method for amplifying the nucleic acid are not particularly limited, and the method can be carried out using conventionally known techniques.

In the production of the amplification product from the template nucleic acid, it is preferable to use a primer for amplifying a region including a detection target polymorphism in the EGFR gene. The sequence of the primer is not particularly limited as long as a detection target sequence including the detection target site can be amplified, for example, and the sequence of the primer can be set as appropriate by a conventionally known method, depending on the detection target sequence, sequences in the vicinity thereof, and the like. The length of the primer is not particularly limited, and can be set to a general length. For example, the length of the primer may be 10- to 30-mer.

As the primer, for example, either one of a forward primer (hereinafter also referred to as "F primer") for amplifying the sense strand of the gene and a reverse primer (hereinafter also referred to as "R primer") for amplifying the antisense strand of the gene may be used. It is preferable to use a primer set including a pair composed of these primers. Examples of the F primer and the R primer are shown below. It is to be noted that they are merely illustrative and by no means limit the present invention.

```
F primer
                                            (SEQ ID NO: 5)
5'-tccaggaagcctacgtgatggccag-3'

R primer
                                            (SEQ ID NO: 6)
5'-ccaatattgtctttgtgttcccggacatagtc-3'

(SEQ ID NO: 7)
5'-cgaagggcatgagctgcg-3'

(SEQ ID NO: 8)
5'-ccgaagggcatgagctgca-3'
```

The R primer of SEQ ID NO: 7 is, for example, a primer for specifically amplifying the wild-type EGFR gene. The R primer of SEQ ID NO: 8 is, for example, a primer for specifically amplifying the mutant-type EGFR gene. The primer of the SEQ ID NO: 7 and the primer of SEQ ID NO: 8 may be used in combination, for example. The primers of SEQ ID NOs: 5 to 8 above also are referred to as the primers of the present invention.

The combination of the primers is not particularly limited. Specific examples thereof include: the combination of the primer of SEQ ID NO: 5 and the primer of SEQ ID NO: 6; and the combination of the primer of SEQ ID NO: 7 and the primer of SEQ ID NO: 8.

In the reaction system, the proportion of the primer to be added is not particularly limited. For example, the proportion of one kind of primer to be added in the reaction system is, for example, 0.1 to 2 µmol/l, preferably 0.25 to 1.5 µmol/l, and particularly preferably 0.5 to 1 µmol/l. When a F primer and a R primer are used, the ratio (the molar ratio F:R) between the F primer (F) and R primer (R) to be added is not particularly limited, and preferably is 1:0.25 to 1:4, more preferably 1:0.5 to 1:2, for example.

In the step (A), the ratio (molar ratio) of the probe to be added relative to the test nucleic acid is not particularly limited. It preferably is 1 or less, more preferably 0.1 or less, because this allows detection signals to be secured sufficiently. At this time, the amount of the test nucleic acid may be, for example, the total amount of a perfect match nucleic acid having a perfect match sequence and a mismatch nucleic acid having a mismatch sequence, or may be the total amount of an amplification product containing a perfect match sequence and an amplification product containing a mismatch sequence. Although the proportion of the perfect match nucleic acid in the test nucleic acid generally is unknown, it is preferable that the ratio (molar ratio) of the probe to be added relative to the perfect match nucleic acid (the amplification product containing the perfect match sequence) eventually becomes 10 or less, more preferably 5 or less, and still more preferably 3 or less. Furthermore, the lower limit of the ratio is not particularly limited, and is, for example, 0.001 or more, preferably 0.01 or more, and more preferably 0.1 or more. The ratio of the probe of the present invention to be added relative to the test nucleic acid may be the molar ratio thereof relative to a double-stranded nucleic acid or relative to a single-stranded nucleic acid, for example.

The proportion of the probe of the present invention to be added in the reaction system is not particularly limited. For example, it is preferable to add the probe so that its concentration is in the range from 10 to 1000 nmol/l, more preferably from 20 to 500 nmol/l. Furthermore, in the reaction system, the molar ratio of the probe relative to the test nucleic acid preferably is, for example, 1 or less, more preferably 0.1 or less, because this allows sufficient signal values to be secured, for example. The ratio of the probe to be added relative to the test nucleic acid may be the molar ratio thereof relative to a double-stranded nucleic acid or relative to a single-stranded nucleic acid, for example.

A sample to which the polymorphism detection method of the present invention is applied is not particularly limited, and examples thereof include biological samples. Specific examples of the biological samples include: whole blood; blood cells such as leukocyte cells; oral cells such as oral mucosa; somatic cells such as nails and hairs; germ cells; sputum; amniotic fluid; paraffin-embedded tissues; urine; gastric juice; and liquid obtained by gastrolavage. In the present invention, a method for collecting the sample, a method for preparing a test nucleic acid from the sample, and the like are not limited, and any conventionally known methods can be employed.

The polymorphism detection method of the present invention can be utilized in so-called Tm analysis such as described above. The following is an explanation of a Tm value in the Tm analysis. For example, when a solution containing a double-stranded DNA is heated, an absorbance at 260 nm increases. This is caused by the fact that the hydrogen bond between the strands composing the double-stranded DNA is unbound by the heating, whereby the double-stranded DNA is dissociated into single-stranded DNAs (melting of DNA). Then, when every double-stranded DNA is dissociated into single-stranded DNAs, the absorbance of the solution becomes about 1.5 times as large as the absorbance at the time when the heating was initiated (i.e., the absorbance of the solution containing only the double-stranded nucleic acid), whereby it can be determined that the melting is completed. Based on this phenomenon, a melting temperature Tm generally is defined as a temperature at the time when the amount of increase in absorbance reaches 50% of the total amount of increase in absorbance.

In the step (A), the measurement of a signal indicating the melting state of a hybrid of the test nucleic acid and the probe may be, for example, the measurement of an absorbance at 260 nm as described above or the measurement of a signal of the labeling substance. Specifically, it is preferable that a labeled probe labeled with the labeling substance is used as the probe as described above and that a signal of the labeling substance is measured. The labeled probe may be, for example, a labeled probe that shows signals independently and shows no signals when it forms a hybrid, or a labeled probe that shows no signals independently and shows signals when it forms a hybrid. The former probe does not show signals when it forms a hybrid (double-stranded DNA) with the amplification product and shows signals when the probe is dissociated from the amplification product by heating. On the other hand, the latter probe shows signals when it forms a hybrid (double-stranded DNA) with the amplification product, and the signals are reduced (quenched) when the probe is dissociated from the amplification product by heating. Therefore, by detecting signals of the labeling substance, the detection of the progress of the melting of the hybrid, the determination of the Tm value, and the like can be achieved, as in the case where the absorbance at 260 nm is measured. The signal of the labeling substance may be detected under the condition specific to the signal of the labeling substance, for example. Examples of the condition include an excitation wavelength and a detection wavelength. The labeled probe and the labeling substance are as described above.

Next, the polymorphism detection method of the present invention will be described with reference to an illustrative example. The present example is directed to the case where the probe of the present invention is a labeled probe labeled with a fluorescent substance, a template nucleic acid is amplified in the presence of the probe, and the resultant amplification product is used as the test nucleic acid. The method of the present invention is characterized in that the probe of the present invention is used in the method, and other steps and conditions are by no means limited.

First, genome DNA is isolated from the biological sample. Isolation of the genome DNA from the biological sample can be achieved by a conventionally known method. As a specific example, the isolation can be achieved using a commercially available genome DNA isolation kit (GFX Genomic Blood DNA Purification kit™; GE Healthcare Bio-Sciences) or the like, for example.

Next, a reaction solution is prepared by adding a labeled probe to a sample containing the isolated genome DNA. As the labeled probe, for example, QProbe® is preferable, as described above.

The labeled probe may be added to the sample containing the isolated genome DNA or may be mixed with the genome DNA in a solvent, for example. The solvent is not particularly limited, and examples thereof include conventionally known solvents including: buffer solutions such as Tris-HCl; solvents respectively containing KCl, $MgCl_2$, $MgSO_4$, glycerol, and the like; and reaction solutions for nucleic acid amplification, such as reaction solutions for PCR.

The timing of adding the labeled probe is not particularly limited. For example, the labeled probe may be added before, during, or after the nucleic acid amplification reaction. In particular, it is preferable to add the labeled probe to the reaction solution before the nucleic acid amplification reaction because, for example, it is not necessary to expose the reaction solution to the external environment in order to add the labeled probe and it is possible to carry out the nucleic acid amplification reaction and the measurement of signal values successively. In this case, it is preferable that the 3' end of the labeled probe is modified with the labeling substance or a phosphate group, as described above.

Subsequently, using the isolated genome DNA as a template, a detection target sequence including a detection target polymorphism is amplified in the presence of the labeled probe by a nucleic acid amplification method such as PCR. Although the following description is directed to the case where PCR is used as the nucleic acid amplification method, the present invention is not limited thereto. Also, conditions for the PCR are not particularly limited, and the PCR can be carried out according to a conventionally known method.

Specifically, the reaction solution containing the genome DNA, the labeled probe, and the primer is subjected to PCR. The composition of the reaction solution is not particularly limited, and those skilled in the art can set the composition as appropriate. In addition to the genome DNA, the labeled probe, and the primer, the reaction solution further may contain: a polymerase such as DNA polymerase; nucleoside triphosphate; a buffer solution; any of various kinds of catalysts; and the like, for example. The proportions of the labeled probe and the primer to be added in the reaction solution are not particularly limited, and they may be in the above-described ranges, respectively, for example.

The DNA polymerase is not particularly limited, and conventionally known polymerases derived from heat-resistant bacteria can be used, for example. As specific examples of such polymerases, *Thermus aquaticus*-derived DNA polymerases (U.S. Pat. Nos. 4,889,818 and 5,079,352 (Taqpolymerase™), *Thermus thermophilus*-derived DNA polymerase (WO 91/09950 (rTth DNA polymerase), *Pyrococcus furiosus*-derived DNA polymerase (WO 92/9689 (Pfu DNA polymerase: Stratagenes), *Thermococcus litoralis*-derived polymerase (EP-A 455 430 (Vent™): New England Biolabs), and the like, for example, are commercially available. Among them, *Thermus aquaticus*-derived heat-resistant DNA polymerases are preferable.

The proportion of the DNA polymerase to be added in the reaction solution is not particularly limited, and is, for example, 1 to 100 U/ml, preferably 5 to 50 U/ml, and more preferably 20 to 40 U/ml. With regard to the unit of activity (U) of DNA polymerases, 1 U generally is defined as an activity for incorporating 10 nmol of entire nucleotide into acid-insoluble precipitate at 74° C. in 30 minutes in a reaction solution for activity measurement using activated salmon sperm DNA as a template primer. The composition of the reaction solution for activity measurement is as follows, for example: 25 mmol/l TAPS buffer (pH 9.3, 25° C.), 50 mmol/l KCL, 2 mmol/l $MgCl_2$, 1 mmol/l mercaptoethanol, 200 μmol/l dATP, 200 μmol/l dGTP, 200 μmol/l dTTP, 100 μmol/l [$\alpha$-$^{32}$P] dCTP, and 0.25 mg/mL activated salmon sperm DNA.

The nucleoside triphosphate generally is dNTP (dATP, dCTP, dGTP, and dTTP or dUTP). The proportion of dNTP to be added in the reaction solution is not particularly limited, and is, for example, 0.01 to 1 mmol/l, preferably 0.05 to 0.5 mmol/l, and more preferably 0.1 to 0.3 mmol/l.

Examples of the buffer solution include Tris-HCl, Tricine, MES, MOPS, HEPES, and CAPS, and it is possible to use commercially available buffer solutions for PCR and buffer solutions included in commercially available PCR kits.

The reaction solution further may contain heparin, betaine, KCl, $MgCl_2$, $MgSO_4$, glycerol, or the like, and the proportions of these components to be added may be set within ranges where they do not interfere with the PCR reaction.

The total volume of the reaction solution is not particularly limited, and can be determined as appropriate depending on a device to be used, such as a thermal cycler, and the like, for example. The total volume generally is 1 to 500 μl, preferably 10 to 100 μl.

Next, PCR is conducted. The cycle conditions of the PCR are not particularly limited. As a specific example, for (1) dissociation of a double-stranded DNA as the test nucleic acid into single-stranded DNAs; (2) annealing of the primer to the single-stranded DNA; and (3) elongation of the primer through a polymerase reaction, conditions shown in Table 1 below can be employed, for example. The number of cycles in the PCR is not particularly limited. It preferably is 30 cycles or more with the three steps described in the following items (1) to (3) as one cycle, for example. The upper limit of the total number of cycles is not particularly limited, and is, for example, 100 cycles or less, preferably 70 cycles or less, and more preferably 50 cycles or less. The temperature change in each of the steps can be controlled automatically using a thermal cycler or the like, for example.

TABLE 1

| | Temperature (° C.) and Time (seconds) |
|---|---|
| (1) Dissociation into single-stranded DNAs | e.g., 90° C. to 99° C., 1 to 120 seconds preferably, 92° C. to 95° C., 1 to 60 seconds |
| (2) Annealing of primer | e.g., 40° C. to 70° C., 1 to 300 seconds preferably, 50° C. to 70° C., 5 to 60 seconds |

TABLE 1-continued

| | Temperature (° C.) and Time (seconds) |
|---|---|
| (3) Elongation of primer | e.g., 50° C. to 80° C., 1 to 300 seconds preferably, 50° C. to 75° C., 5 to 60 seconds |

The proportion of the labeled probe to be added in the reaction solution is not particularly limited. For example, it is preferable to add the labeled probe so that its concentration is in the range from 10 to 1000 nmol/l, more preferably from 20 to 500 nmol/l. In the reaction solution, the molar ratio of the labeled probe relative to the test nucleic acid preferably is, for example, 1 or less, more preferably 0.1 or less, because this allows sufficient signal values to be secured, for example. The ratio of the labeled probe to be added relative to the test nucleic acid may be the molar ratio thereof relative to a double-stranded nucleic acid or relative to a single-stranded nucleic acid, for example.

Next, disassociation of the obtained amplification product (double-stranded DNA) and hybridization of the labeled probe with a single-stranded DNA obtained through the disassociation are caused. They can be achieved by, for example, changing the temperature of the reaction solution in the presence of the labeled probe. In this case, it is preferable that the reaction solution to which the labeled probe has been added is subjected to an amplification reaction, after which the temperature of the reaction solution is changed, as described above.

The heating temperature in the disassociation step may be, for example, a temperature at which the double-stranded amplification product can be disassociated into single strands. The heating temperature is not particularly limited, and is, for example, 85° C. to 95° C. The heating time is not particularly limited, and generally is 1 second to 10 minutes, preferably 1 second to 5 minutes.

The hybridization of the labeled probe with the disassociated single-stranded DNA can be achieved by, for example, lowering the heating temperature in the disassociation step after the completion of the disassociation step. The temperature condition is, for example, 40° C. to 50° C. The time period for conducting a treatment at this temperature is not particularly limited, and is, for example, 1 to 600 seconds.

Then, signal values indicating the melting states of the hybrid of the amplification product and the labeled probe are measured while changing the temperature of the reaction solution. Specifically, for example, the reaction solution is heated, in other words, the hybrid of the single-stranded DNA and the labeled probe is heated, and change in signal value accompanying the temperature rise is measured. As described above, in the case where a guanine quenching probe, i.e., a probe in which cytosine (c) at the end is labeled, is used, fluorescence is reduced (or quenched) in the state where the probe hybridizes with the single-stranded DNA, and fluorescence is emitted in the state where the probe is disassociated. Therefore, in this case, the hybrid with reduced (quenched) fluorescence may be heated gradually, and increase in fluorescence intensity accompanying the temperature rise may be measured, for example.

When measuring the change in fluorescence intensity, the temperature range used in the measurement is not particularly limited. The initiation temperature is, for example, room temperature to 85° C., preferably 25° C. to 70° C., and the end temperature is, for example, 40° C. to 105° C. The temperature rising rate is not particularly limited, and is, for example, 0.1 to 20° C./sec., preferably 0.3 to 5° C./sec.

Next, the Tm value is determined by analyzing the change in signal value. Specifically, from the obtained fluorescence intensities, the amount of change in fluorescence intensity per unit time (−d amount of change in fluorescence intensity/dt or d amount of change in fluorescence intensity/dt) at each temperature is calculated, and a temperature at which the amount of change is largest can be determined as the Tm value. When the labeled probe is the fluorescence quenching probe, the Tm value can be determined in the following manner, for example: the amount of increase in fluorescence intensity is measured, and a temperature at which the amount of increase in fluorescence intensity per unit time (−d amount of increase in fluorescence intensity/dt) is smallest or a temperature at which the amount of increase in fluorescence intensity per unit time (d amount of increase in fluorescence intensity/t) is largest can be determined as the Tm value. On the other hand, when a probe that shows no signals independently and shows signals when it forms a hybrid is used as the labeled probe instead of the fluorescence quenching probe, the amount of decrease in fluorescence intensity may be measured, contrary to the case stated above.

The Tm value can be calculated using MELTCALC software (http://www.meltcalc.com/), which is known conventionally, or the like, for example. Also, the Tm value can be determined by a nearest neighbor method.

Then, based on the Tm value, it is determined whether the 347th base in the partial sequence of the EGFR gene shown in SEQ ID NO: 1 is of the wild type or the mutant type in the detection target sequence. In the Tm analysis, for example, a perfectly complementary hybrid (match) exhibits a higher Tm value, which indicates dissociation, than a hybrid with one or more different bases (mismatch). Therefore, with regard to the labeled probe, the Tm value of a perfect match hybrid and the Tm value of a mismatch hybrid are determined beforehand. The former is the Tm value of a perfect match hybrid in which the label probe is perfectly complementary to the detection target sequence except for the 17th base (g) in SEQ ID NO: 2. The latter is the Tm value of a mismatch hybrid in which the label probe is perfectly complementary to the detection target sequence except for the 9th base (r) and the 17th base (g) in SEQ ID NO: 2, i.e., the Tm value of a hybrid in which the mismatch occurs at the 9th base (r) and the 17th base (g) in the label probe. Based on the thus-determined Tm values, it is possible to determine the base in the detection target sequence is of the wild type or the mutant type.

In the present invention, instead of raising the temperature of the reaction system containing the probe, in other words, heating the hybrid, and then measuring the change in signal accompanying the temperature rise as described above, the change in signal at the time of hybrid formation may be measured, for example. That is, when forming a hybrid by lowering the temperature of the reaction system containing the probe, the change in signal accompanying the temperature lowering may be measured.

As a specific example, the case where a labeled probe that shows signals independently and shows no signals when it forms a hybrid (e.g., a guanine quenching probe) is used will be described. In this case, the labeled probe emits fluorescence in the state where a single-stranded DNA and the labeled probe are dissociated, and the fluorescence is reduced (or quenched) when the temperature is lowered to allow the labeled probe to form a hybrid. Therefore, in this case, the temperature of the reaction solution may be lowered gradually, and decrease in fluorescence intensity accompanying the temperature lowering may be measured, for example. On the other hand, when a labeled probe that shows no signals independently and shows signals when it forms a hybrid is used, the labeled probe does not emit fluorescence in the state where the single-stranded DNA and the labeled probe are dissociated, and the labeled probe emits fluorescence when the temperature is lowered to allow the labeled probe to form a hybrid. Therefore, in this case, the temperature of the reaction solution may be lowered gradually, and increase in fluorescence intensity accompanying the temperature lowering may be measured, for example.

<Reagent for Detection Polymorphism>

The reagent for detecting a polymorphism of the present invention is a reagent for detecting a polymorphism in an EGFR gene, containing the probe of the present invention. The reagent of the present invention is characterized in that it contains the above-described probe of the present invention, and other configurations and conditions are by no means limited.

The reagent of the present invention further may contain a primer or a primer set for amplifying a region including the detection target site in the EGFR gene. Examples of the primer include those described above.

The reagent of the present invention further may contain components necessary for the nucleic acid amplification reaction, for example. Specific examples of such components include: polymerases such as DNA polymerases; nucleoside triphosphate; buffer solutions; and various kinds of catalysts. In the reagent of the present invention, the respective components may be contained in the same container or separate containers, for example.

The reagent of the present invention also can be referred to as a probe kit for use in the detection of the polymorphism in the EGFR gene, for example. In the kit of the present invention, the respective components may be contained in the same container or separate containers, for example. The kit of the present invention further may include instructions for use.

The primer for amplifying an EGFR gene according to the present invention is as described above, and is at least one of the primers composed of the oligonucleotides of SEQ ID NOs: 5 to 8. An amplification method according to the present invention is a method for amplifying an EGFR gene, including the step of amplifying an EGFR gene with a nucleic acid in a sample as a template in a reaction system using the primer for amplifying an EGFR gene according to the present invention. A method for detecting an amplification product according to the present invention is a method for detecting an amplification product of an EGFR gene, including the step of: amplifyiying an EGFR gene by the method for amplifying an EGFR gene according to the present invention using the primer of the present invention. The detection method according to the present invention preferably further includes the step of: detecting the amplification product of the EGFR gene using the probe of the present invention, for example. Regarding the primer of the present invention and the methods using the primer, the above descrptions can be referred to.

Next, examples of the present invention will be described. It is to be noted, however, the present invention is by no means limited by the following examples. In the following examples, "%" means "w/v %" unless otherwise stated.

EXAMPLES

Example 1

In the present example, polymorphisms in EGFR genes were detected by carrying out Tm analysis in the presence of a wild-type plasmid and a mutant-type plasmid.

A wild-type plasmid (wt) and a mutant-type plasmid (mt) were produced. The wt was a plasmid obtained through insertion of a partial sequence (from 197th to 496th bases in SEQ ID NO: 1) of a wild-type EGFR gene in which the 347th base y in SEQ ID NO: 1 was cytosine (c). The mt was a plasmid obtained through insertion of a partial sequence (from 197th to 496th base in SEQ ID NO: 1) of a mutant-type EGFR gene in which the 347th base y in SEQ ID NO: 1 was mutated to thymine (t). They were mixed together at predetermined mixing ratios, thus preparing a plurality kinds of nucleic acid samples. The contents of the mt in the nucleic acid samples were 5%, 3%, and 0%, respectively.

1 µl ($1\times10^3$ to $1\times10^4$ copies/µl of each nucleic acid sample and 49 µl of a reaction reagent shown in Table 2 below were added to a tube, thus providing a PCR reaction solution. The PCR reaction solution was subjected to PCR and Tm analysis using a fully-automated SNP analyzer (i-densy®, ARKRAY, Inc.). The PCR was carried out in the following manner: the PCR reaction solution was first treated at 95° C. for 60 seconds, then was subjected to 50 cycles of treatment with a treatment at 95° C. for 1 second and at 62° C. for 15 seconds as one cycle, and further was treated at 95° C. for 1 second and 40° C. for 60 seconds. Subsequently, the Tm analysis was carried out by heating the PCR reaction solution from 40° C. to 75° C. at a temperature rising rate of 1° C./3 seconds and measuring the change in fluorescence intensity (the detection wavelength: from 565 to 605 nm) with time.

TABLE 2

| (Composition of PCR reaction solution: unit µl) | |
| --- | --- |
| distilled water | 36.46 |
| 1 mol/l Tris-HCl (pH 8.6) | 1.25 |
| 20% BSA | 0.50 |
| 10% NaN$_3$ | 0.23 |
| 2.5 mmol/l dNTP | 4.00 |
| 80% glycerol | 1.56 |
| 100 mol/l MgCl$_2$ | 0.75 |
| 1 mol/l KCl | 1.25 |
| 100 µmol/l F primer | 0.50 |
| 100 µmol/l R primer | 0.25 |
| 5 µmol/l probe for polymorphism detection | 2.00 |
| 5 U/µl Gene Taq (NIPPON GENE) | 0.25 |
| Total | 49 µl |

As the F primer and the R primer, primers having the following sequences were used, respectively.

```
F primer 1
                                       (SEQ ID NO: 5)
5'-tccaggaagcctacgtgatggccag-3'

R primer 1
                                       (SEQ ID NO: 6)
5'-ccaatattgtctttgtgttcccggacatagtc-3'
```

As the probe for polymorphism detection, a probe having the following sequence was used. The sequence of the probe showed a perfect match with the sense strand of the mutant-type EGFR gene in which the 347th base y in SEQ ID NO: 1 was mutated to thymine (t), except for the 17th base (g). In the following sequence, the base A indicated with a capital letter is to be paired with the 347th base thymine (t). Furthermore, TAMRA at the 3' end represents a fluorescent substance.

```
Probe 1 for polymorphism detection
                                       (SEQ ID NO: 3)
5'-tgagctgcAtgatgaggtgcac-(TAMRA)-3'
```

Figure 1B:
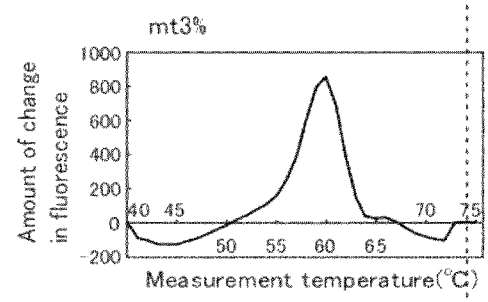
Figure 1C:
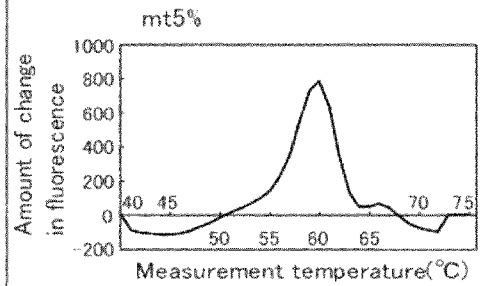

The results thereof are shown in FIGS. 1A to 1C. FIGS. 1A to 1C are graphs showing the Tm analysis results and indicate the change in fluorescence intensity accompanying the temperature rise. FIG. 1A shows the result obtained when the nucleic acid sample in which the content of the wt was 100% (the content of the mt was 0%) was used, FIG. 1B shows the result obtained when the nucleic acid sample in which the content of the mt was 3% was used, and FIG. 1C shows the result obtained when the nucleic acid sample in which the content of the mt was 5% was used. The horizontal axis indicates a temperature (° C.) at the time of measurement. The vertical axis indicates the change in fluorescence intensity (hereinafter also referred to as the "amount of change in fluorescence"), and the unit thereof is "d amount of increase in fluorescence intensity/dt". In the case where the formed hybrid shows a perfect match with the probe except for the 17th base (g), the Tm serving as an evaluation standard value is as follows: the Tm value of the wt is 59° C. and the Tm value of the mt is 66° C.

As can be seen from FIG. 1A, with regard to the sample in which the content of the wt was 100%, a peak was observed only at the Tm value of the wt. Furthermore, as can be seen from FIGS. 1B and 1C, with regard to the reaction solutions containing the mutant-type plasmid, peaks were observed both at the Tm value of the wt and at the Tm value of the mt. As described above, it was found that, even when the sample contained both the wt and the mt, the probe according to the present example could detect both the polymorphisms. Furthermore, when the content of the mt in the sample was small, a peak was observed at the Tm value of the mt. This demonstrates that, according to the probe of the present example, even in the case where the content of the mt is small, it is possible to detect the mutant-type polymorphism with high sensitivity.

Example 2

In the present example, polymorphisms of the EGFR gene were detected by carrying out Tm analysis in the presence of a wild-type plasmid (wt) and a mutant-type plasmid (mt) that was contained at concentrations still lower than those in Example 1.

In the present example, PCR and Tm analysis were carried out in the same manner as in Example 1, except that: the contents of the mt in the nucleic acid samples were set to 0.5%, 0.3%, and 0%, respectively; as the above-described R primer, 0.125 µl of 100 µmol/l R primer 2 and R primer 3 shown below were added, respectively; and the PCR was carried out under the following condition: the PCR reaction solutions were first treated at 95° C. for 60 seconds, then were subjected to 50 cycles of treatment with a treatment at 95° C. for 1 second and at 64° C. for 15 seconds as one cycle, and further were treated at 95° C. for 1 second and 40° C. for 60 seconds.

```
R primer 2
                                       (SEQ ID NO: 7)
5'-cgaagggcatgagctgcG-3'

R primer 3
                                       (SEQ ID NO: 8)
5'-ccgaagggcatgagctgcA-3'
```

The R primer 2 was a primer for amplifying the wild-type EGFR gene, and the R primer 3 was a primer for amplifying the mutant-type EGFR gene. In each of the R primer 2 and the R primer 3, the base at the 3' end is to be paired with the 347th base (y=c, t) in the sequence of SEQ ID NO: 1.

Figure 2A:
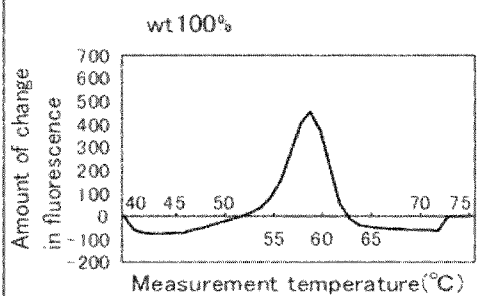
FIGS. 2A to 2C are graphs showing the results of Tm analysis obtained in Example 2 of the present invention.
Figure 2B:
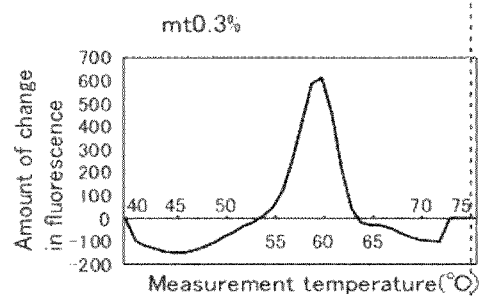
Figure 2C:
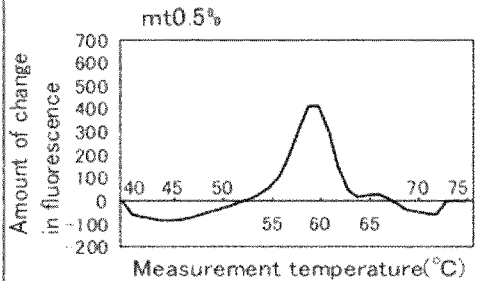

The results thereof are shown in FIGS. 2A to 2C. FIGS. 2A to 2C are graphs showing the Tm analysis results and indicate the change in fluorescence intensity accompanying the temperature rise. FIG. 2A shows the result obtained with regard to the nucleic acid sample in which the content of the wt was 100% (the content of the mt was 0%), FIG. 2B shows the result obtained with regard to the nucleic acid sample in which the content of the mt was 0.3%, and FIG. 2C shows the result obtained with regard to the nucleic acid sample in which the content of the mt was 0.5%. The horizontal axis indicates a temperature (° C.) at the time of measurement. The vertical axis indicates the change in fluorescence intensity (the amount of change in fluorescence), and the unit thereof is "d amount of increase in fluorescence intensity/dt". The Tm serving as an evaluation standard value is the same as described above, namely, as follows: the Tm value of the wt is 59° C. and the Tm value of the mt is 66° C.

As can be seen from FIG. 2A, with regard to the sample in which the content of the wt was 100%, a peak was observed only at the Tm value of the wt. Furthermore, as can be seen from FIGS. 2B and 2C, with regard to the reaction solutions containing the mutant-type plasmid, peaks were observed both at the Tm value of the wt and at the Tm value of the mt. As described above, even when the sample contained both the wt and the mt, the probe according to the present example could detect both the polymorphisms. Furthermore, when the content of the mt in the sample was still smaller, a peak was observed at the Tm value of the mt. That is, in the present example, even in the case where the content of the mutant-type plasmid was still smaller than those in Example 1, it was possible to analyze the mutant-type polymorphism with high sensitivity.

Comparative Example

In the present example, polymorphisms in EGFR genes were detected in the same manner as in Example 1, except that each of the following probes 2 to 7 for polymorphism detection was used as the above-described probe.

Probe 2
(SEQ ID NO: 9)
5'-(TAMRA)-catgagctgcAtgatgag-P-3'

Probe 3
(SEQ ID NO: 10)
5'-(TAMRA)-catgagctgcAtgatgaggtgca-P-3'

Probe 4
(SEQ ID NO: 11)
5'-ctgcAtgatgaggtgcac-(TAMRA)-3'

Probe 5
(SEQ ID NO: 12)
5'-(TAMRA)-catcaTgcagctcat-P-3'

Probe 6
(SEQ ID NO: 13)
5'-(TAMRA)-catcaTgcagctca-P-3'

Probe 7
(SEQ ID NO: 14)
5'-(TAMRA)-ctcatcaTgcagct-P-3'

When each of the probes 2 to 7 was used as the above-described probe, in the Tm analysis with respect to all the PCR reaction solutions containing the nucleic acid sample in which the content of the wt was 100%, the nucleic acid sample in which the content of the mt was 3%, and the nucleic acid sample in which the content of the mt was 5%, respectively, the fluorescence was not quenched so that the peak of the amount of change in fluorescence was not observed. That is, when the probes according to the present example were used, the polymorphisms in the EGFR gene could not be detected by the Tm analysis.

Industrial Applicability

As specifically described above, according to the present invention, a polymorphism in the EGFR gene can be identified easily and with high reliability by Tm analysis, for example. Therefore, the present invention is particularly useful when applied to a sample containing both a normal EGFR gene and a mutant-type EGFR gene. Thus, according to the present invention, a polymorphism in the EGFR gene can be identified easily and with high reliability, so that, for example, the detection result can be reflected in treatments carried out by administration of an anticancer drug, such as described above. Hence, it can be said that the present invention is very useful in a medical field and the like.

While the present invention has been described with reference to iilustrative embodiments and examples, it is to be understood that changes and modifications that may become apparent to those skilled in the art may be made without departing from the scope of the present invention.

The invention claimed is:

1. A probe for detecting a polymorphism in an EGFR gene, the probe comprising a label and either one of an oligonucleotide (P1) and an oligonucleotide (P2), wherein:
   (P1) is an oligonucleotide consisting of a base sequence of any one of SEQ ID NO: 2, SEQ ID NO: 15, SEQ ID NO: 16, and SEQ ID NO: 17; and
   (P2) is an oligonucleotide consisting of a base sequence complementary to the oligonucleotide (P1) and
   the label comprises a fluorescent labeling substance.

2. The probe according to claim 1, wherein
   the oligonucleotide (P1) has the fluorescent labeling substance in its 3' end region.

3. The probe according to claim 1, wherein
   the oligonucleotide (P1) has the fluorescent labeling substance at a position of 1st to 4th bases from its 3' end.

4. The probe according to claim 1, wherein the probe is a probe for use in Tm analysis.

5. A method for detecting a polymorphism in an EGFR gene, the method comprising the step of:
   detecting a polymorphism in an EGFR gene using the probe according to claim 1.

6. The method according to claim 5, wherein the detecting step comprises the steps of:

(A) while changing a temperature of a reaction system containing a test nucleic acid and the probe according to claim 1, measuring a signal value indicating a melting state of a hybrid of the test nucleic acid and the probe; and
(B) determining the polymorphism in the test nucleic acid based on a change in the signal value accompanying the temperature change.

7. The method according to claim 6, wherein, in the step (A), the test nucleic acid is an amplification product obtained by amplifying a template nucleic acid.

8. The method according to claim 7, further comprising the step of:
   producing the amplification product from the template nucleic acid.

9. The method according to claim 8, wherein
Step (A) further comprises the step of producing the nucleic acid amplification product from the template nucleic acid in a reaction system in the presence of the probe, and wherein the signal value is measured while changing a temperature of the reaction system in the step of producing the nucleic acid amplification product.

10. The probe according to claim 1, wherein
   the oligonucleotide (P2) has the fluorescent labeling substance in its 5' end region.

11. The probe according to claim 1, wherein the oligonucleotide (P2) has the fluorescent labeling substance at a position of 1st to 4th bases from its 5' end.

* * * * *

SEQUENCE LISTING

<160> NUMBER OF SEQ ID NOS: 23

<210> SEQ ID NO 1
<211> LENGTH: 1020
<212> TYPE: DNA
<213> ORGANISM: Homo sapiens

<400> SEQUENCE: 1

| | | | | | |
|---|---|---|---|---|---|
| tggccactgt | tgcctgggcc | tctctgtcat | ggggaatccc | cagatgcacc | caggaggggc | 60 |
| cctctcccac | tgcatctgtc | acttcacagc | cctgcgtaaa | cgtccctgtg | ctaggtcttt | 120 |
| tgcaggcaca | gctttttcctc | catgagtacg | tattttgaaa | ctcaagatcg | cattcatgcg | 180 |
| tcttcacctg | gaagggtcc | atgtgcccct | ccttctggcc | accatgcgaa | gccacactga | 240 |
| cgtgcctctc | cctccctcca | ggaagcctac | gtgatggcca | gcgtggacaa | cccccacgtg | 300 |

-continued

```
tgccgcctgc tgggcatctg cctcacctcc accgtgcagc tcatcaygca gctcatgccc    360
ttcggctgcc tcctggacta tgtccgggaa cacaaagaca atattggctc ccagtacctg    420
ctcaactggt gtgtgcagat cgcaaaggta atcaggaag ggagatacgg ggaggggaga     480
taaggagcca ggatcctcac atgcggtctg cgctcctggg atagcaagag tttgccatgg    540
ggatatgtgt gtgcgtgcat gcagcacaca cacattcctt tattttggat tcaatcaagt    600
tgatcttctt gtgcacaaat cagtgcctgt cccatctgca tgtggaaact ctcatcaatc    660
agctaccttt gaagaatttt ctctttattg agtgctcagt gtggtctgat gtctctgttc    720
ttatttctct ggaattcttt gtgaatactg tggtgatttg tagtggagaa ggaatattgc    780
ttcccccatt caggacttga taacaaggta agcaagccag gccaaggcca ggaggaccca    840
ggtgatagtg gtggagtgga gcaggtgcct tgcaggaggc ccagtgagga ggtgcaagga    900
gctgacagag ggcgcagctg ctgctgctat gtggctgggg ccttggctaa gtgtcccct    960 ttccacaggc tcgctccaga gccagggcgg ggctgagaga gcagagtggt caggtagccc   1020

<210> SEQ ID NO 2
<211> LENGTH: 22
<212> TYPE: DNA
<213> ORGANISM: Artificial
<220> FEATURE:
<223> OTHER INFORMATION: probe

<400> SEQUENCE: 2
tgagctgcrt gatgaggtgc ac                                              22

<210> SEQ ID NO 3
<211> LENGTH: 22
<212> TYPE: DNA
<213> ORGANISM: Artificial
<220> FEATURE:
<223> OTHER INFORMATION: probe

<400> SEQUENCE: 3
tgagctgcat gatgaggtgc ac                                              22

<210> SEQ ID NO 4
<211> LENGTH: 22
<212> TYPE: DNA
<213> ORGANISM: Artificial
<220> FEATURE:
<223> OTHER INFORMATION: probe

<400> SEQUENCE: 4
tgagctgcgt gatgaggtgc ac                                              22

<210> SEQ ID NO 5
<211> LENGTH: 25
<212> TYPE: DNA
<213> ORGANISM: Artificial
<220> FEATURE:
<223> OTHER INFORMATION: primer

<400> SEQUENCE: 5
tccaggaagc ctacgtgatg gccag                                           25

<210> SEQ ID NO 6
<211> LENGTH: 32
<212> TYPE: DNA
<213> ORGANISM: Artificial
<220> FEATURE:
<223> OTHER INFORMATION: primer
```

```
<400> SEQUENCE: 6
ccaatattgt ctttgtgttc ccggacatag tc                                32

<210> SEQ ID NO 7
<211> LENGTH: 18
<212> TYPE: DNA
<213> ORGANISM: Artificial
<220> FEATURE:
<223> OTHER INFORMATION: primer

<400> SEQUENCE: 7
cgaagggcat gagctgcg                                                18

<210> SEQ ID NO 8
<211> LENGTH: 19
<212> TYPE: DNA
<213> ORGANISM: Artificial
<220> FEATURE:
<223> OTHER INFORMATION: primer

<400> SEQUENCE: 8
ccgaagggca tgagctgca                                               19

<210> SEQ ID NO 9
<211> LENGTH: 18
<212> TYPE: DNA
<213> ORGANISM: Artificial
<220> FEATURE:
<223> OTHER INFORMATION: probe

<400> SEQUENCE: 9
catgagctgc atgatgag                                                18

<210> SEQ ID NO 10
<211> LENGTH: 23
<212> TYPE: DNA
<213> ORGANISM: Artificial
<220> FEATURE:
<223> OTHER INFORMATION: probe

<400> SEQUENCE: 10
catgagctgc atgatgaggt gca                                          23

<210> SEQ ID NO 11
<211> LENGTH: 18
<212> TYPE: DNA
<213> ORGANISM: Artificial
<220> FEATURE:
<223> OTHER INFORMATION: probe

<400> SEQUENCE: 11
ctgcatgatg aggtgcac                                                18

<210> SEQ ID NO 12
<211> LENGTH: 15
<212> TYPE: DNA
<213> ORGANISM: Artificial
<220> FEATURE:
<223> OTHER INFORMATION: probe

<400> SEQUENCE: 12
catcatgcag ctcat                                                   15

<210> SEQ ID NO 13
<211> LENGTH: 14
```

```
<210> SEQ ID NO 13
<211> LENGTH: 14
<212> TYPE: DNA
<213> ORGANISM: Artificial
<220> FEATURE:
<223> OTHER INFORMATION: probe

<400> SEQUENCE: 13
catcatgcag ctca                                                         14

<210> SEQ ID NO 14
<211> LENGTH: 14
<212> TYPE: DNA
<213> ORGANISM: Artificial
<220> FEATURE:
<223> OTHER INFORMATION: probe

<400> SEQUENCE: 14
ctcatcatgc agct                                                         14

<210> SEQ ID NO 15
<211> LENGTH: 23
<212> TYPE: DNA
<213> ORGANISM: Artificial
<220> FEATURE:
<223> OTHER INFORMATION: probe

<400> SEQUENCE: 15
tgagctgcrt gatgaggtgc acg                                               23

<210> SEQ ID NO 16
<211> LENGTH: 24
<212> TYPE: DNA
<213> ORGANISM: Artificial
<220> FEATURE:
<223> OTHER INFORMATION: probe

<400> SEQUENCE: 16
tgagctgcrt gatgaggtgc acgg                                              24

<210> SEQ ID NO 17
<211> LENGTH: 25
<212> TYPE: DNA
<213> ORGANISM: Artificial
<220> FEATURE:
<223> OTHER INFORMATION: probe

<400> SEQUENCE: 17
tgagctgcrt gatgaggtgc acggt                                             25

<210> SEQ ID NO 18
<211> LENGTH: 23
<212> TYPE: DNA
<213> ORGANISM: Artificial
<220> FEATURE:
<223> OTHER INFORMATION: probe

<400> SEQUENCE: 18
tgagctgcat gatgaggtgc acg                                               23

<210> SEQ ID NO 19
<211> LENGTH: 23
<212> TYPE: DNA
<213> ORGANISM: Artificial
<220> FEATURE:
<223> OTHER INFORMATION: probe

<400> SEQUENCE: 19
tgagctgcgt gatgaggtgc acg                                               23
```

-continued

```
<210> SEQ ID NO 20
<211> LENGTH: 24
<212> TYPE: DNA
<213> ORGANISM: Artificial
<220> FEATURE:
<223> OTHER INFORMATION: probe

<400> SEQUENCE: 20
tgagctgcat gatgaggtgc acgg                                              24

<210> SEQ ID NO 21
<211> LENGTH: 24
<212> TYPE: DNA
<213> ORGANISM: Artificial
<220> FEATURE:
<223> OTHER INFORMATION: probe

<400> SEQUENCE: 21
tgagctgcgt gatgaggtgc acgg                                              24

<210> SEQ ID NO 22
<211> LENGTH: 25
<212> TYPE: DNA
<213> ORGANISM: Artificial
<220> FEATURE:
<223> OTHER INFORMATION: probe

<400> SEQUENCE: 22
tgagctgcat gatgaggtgc acggt                                             25

<210> SEQ ID NO 23
<211> LENGTH: 25
<212> TYPE: DNA
<213> ORGANISM: Artificial
<220> FEATURE:
<223> OTHER INFORMATION: probe

<400> SEQUENCE: 23
tgagctgcgt gatgaggtgc acggt                                             25
```